United States Patent
Hagedorn et al.

(10) Patent No.: US 8,942,813 B1
(45) Date of Patent: Jan. 27, 2015

(54) TRANSCRANIAL STIMULATION DEVICE AND METHOD BASED ON ELECTROPHYSIOLOGICAL TESTING

(71) Applicant: Evoke Neuroscience, Inc., Jacksonville, NC (US)

(72) Inventors: David W Hagedorn, Jacksonville, NC (US); James W. G. Thompson, New York, NY (US)

(73) Assignee: Evoke Neuroscience, Inc., Jacksonville, NC (US)

( * ) Notice: Subject to any disclaimer, the term of this patent is extended or adjusted under 35 U.S.C. 154(b) by 0 days.

(21) Appl. No.: 14/516,207

(22) Filed: Oct. 16, 2014

Related U.S. Application Data

(63) Continuation of application No. 14/458,673, filed on Aug. 13, 2014, which is a continuation-in-part of application No. 13/742,066, filed on Jan. 15, 2013, now Pat. No. 8,838,247, which is a continuation of application No. 13/543,204, filed on Jul. 6, 2012, now Pat. No. 8,380,316, which is a continuation of application No. 12/979,419, filed on Dec. 28, 2010, now Pat. No. 8,239,030.

(60) Provisional application No. 61/292,791, filed on Jan. 6, 2010.

(51) Int. Cl.
*A61N 1/00* (2006.01)
*A61N 2/00* (2006.01)

(52) U.S. Cl.
CPC .................................... *A61N 2/006* (2013.01)
USPC ........................................................... 607/45

(58) Field of Classification Search
USPC ........................................................... 607/45
See application file for complete search history.

(56) References Cited

U.S. PATENT DOCUMENTS

2008/0319505 A1* 12/2008 Boyden et al. .................. 607/45
2009/0099623 A1* 4/2009 Bentwich ......................... 607/45
2011/0224571 A1* 9/2011 Pascual-Leone et al. ..... 600/544

OTHER PUBLICATIONS

Miranda, P.C., et al., Brain Stimulation Models, Experiments and Open Questions HIVE Deliverable D1.1, Jun. 9, 2009, HIVE: Hyper Interaction Viability Experiments EU FP7 FEY Open—222079.
Riera, Alejandro, et al., Human Brain Stimulation Technologies and Clinical Applications HIVE Deliverable D3.1, May 27, 2010, HIVE: Hyper Interaction Viability Experiments EU FP7 FET Open—222079.

* cited by examiner

*Primary Examiner* — Robert N Wieland
(74) *Attorney, Agent, or Firm* — Bechen PLLC

(57) ABSTRACT

Embodiments of the disclosed technology provide a combination electroencephalography and non-invasive stimulation devices. Upon measuring an electrical anomaly in a region of a brain, various non-invasive stimulation techniques are utilized to correct neural activity. Stimulation techniques include transcranial direct current stimulation, transcranial alternating current stimulation and transcranial random noise stimulation, low threshold transcranial magnetic stimulation and repetitive transcranial magnet stimulation. Devices of the disclosed technology may utilize visual, balance, auditory, and other stimuli to test the subject, analyze necessary brain stimulations, and administer stimulation to the brain.

19 Claims, 6 Drawing Sheets

TRANSCRANIAL STIMULATION DEVICE AND METHOD BASED ON ELECTROPHYSIOLOGICAL TESTING

RELATED APPLICATIONS

The present invention is a continuation of U.S. application Ser. No. 14/458,673, filed Aug. 13, 2014, which is a continuation-in-part of and claims priority to U.S. patent application Ser. No. 13/742,066 filed Jan. 15, 2013, issued as U.S. Pat. No. 8,838,247, which is a continuation of U.S. patent application Ser. No. 13/543,204, filed Jul. 6, 2012, issued as U.S. Pat. No. 8,380,316, which is a continuation of and claims priority to U.S. patent application Ser. No. 12/979,419, filed on Dec. 28, 2010, issued as U.S. Pat. No. 8,239,030, which is based on and claims priority to U.S. Provisional Patent Application Ser. No. 61/292,791 filed Jan. 6, 2010.

COPYRIGHT NOTICE

A portion of the disclosure of this patent document contains material, which is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

FIELD OF INVENTION

The disclosed technology relates generally to the assessment and remediation of abnormal brain and physiological functioning. More specifically, the technology relates to assessing and localizing abnormal brain functioning and heart rate function as well as the concomitant physical dysfunctions that may result.

BACKGROUND

Traumatic brain injuries can result in physical and/or emotional dysfunction. Post traumatic stress disorder (PTSD) symptoms are similar to those of a mild traumatic brain injury (mTBI) and the two are difficult to differentiate using current assessment methodologies such as symptom assessments and questionnaires. In Army deployment, statistics have shown that upwards of 20% of soldiers suffer from mild traumatic brain injury (mTBI). Head and neck injuries, including severe brain trauma, have been reported in one quarter of United States service members who have been evacuated from Iraq and Afghanistan in the first decade of the 21st century A common cause of such injuries arises from exposure to percussive force from explosive devices. Further, recent military analysis indicates that over 90% of patients with acute mTBI will have vestibular (inner ear balance) disorders and those vestibular disorders are present in over 80% of persons with chronic mTBI symptoms. Likewise, stress disorders further affect numerous individuals, whether in a military or civilian situation. Brain injuries may further be incurred from car and bicycle accidents, sports accidents, falls, and the like. Up to 15% of persons suffering even a mild brain injury, or concussion, will suffer from persistent symptoms for more than a year, which significantly negatively affect their ability to work and function in daily life. It is estimated that there are currently 5.3 million Americans living with a disability as a result of a TBI. There are approximately 1.5 million diagnosed brain injuries in the U.S. annually, and it is estimated that another 2 million TBIs occur but are not properly diagnosed. Current assessment methods are either prohibitively expensive or do not diagnose the root cause of the suffering. Thus, there is a need in the art to accurately and quickly assess brain injury and associated dysfunction and then find ways to aid or enhance optimal functioning.

The brain is composed of about 100 billion neurons, more than 100 billion support cells and between 100 and 500 trillion neural connections. Each neuron, support cell and neural connection is extremely delicate, and the neural connections are tiny (approximately 1 micrometer). When the brain moves within the skull, such as occurs in rapid acceleration/deceleration (e.g., exposure to sudden impact and/or explosive devices), axons within the brain can pull, stretch and tear. If there is sufficient injury to the axon or support cells, the cell will die, either immediately or within a few days. Such damage can occur not only in the region that suffered direct trauma but in multiple regions (e.g., diffuse axonal injury). Loss of consciousness is not a prerequisite for mild traumatic brain injury and occurs in less than 5% of mild brain injuries, and head injuries such as diffuse axonal injury are not detectable in routine CT or MRI scan. High false negative findings may lead to patients being undiagnosed or misdiagnosed. Unfortunately current imaging methods still lack the resolution and sensitivity to determine functional brain capacity. Rating scales and other neuropsychological and functional examination methods have long been used to elucidate these functional questions, but they too are fraught with false negative results and limited specificity.

With the high prevalence of age-related cognitive decline conditions, injury from falls, cerebral-vascular events, neurodegenerative conditions (i.e., Alzheimer's Disease) and the many brain injuries occurring in sports and in military operation theaters, there is a need for a rapid and portable assessment instrument that can identify mTBI and neurocognitive dysfunction (e.g., balance, processing speed), direct and provide treatment interventions, track recovery progress, and aid in peak performance or the determination of return to leisure activities or duty.

BRIEF DESCRIPTION

An object of the disclosed technology is to utilize a brain-computer interface with electroencephalography and event-related potential (ERP) measures to localize brain injury and dysfunctional regions.

A further object of the disclosed technology is to provide low intensity direct current stimulation to dysfunctional brain regions as directed by the result(s) of electroencephalography (EEG) and event-related potential (ERP) measures.

Yet another object of the disclosed technology is to provide transcranial current stimulation (tCS) for selective stimulation, based on measures of brain activity and physiological characteristics and measures.

In a method of the disclosed technology, electrophysiological data recording and analysis, with manual or automated delivery of transcranial current stimulation proceeds as follows. Via at least one electrode and at least one reference and ground electrode and, in one or more embodiments, a plurality of electrodes, non-invasive measurements of electrical currents produced by the brain of a person are conducted, including in one embodiment using a low intensity electromagnetic stimulation. This is done while directed stimuli, such as auditory or visual stimuli or balance tasks (for the purpose of examining brain reactions and processing of stimuli) are administered to the person being tested. A brain functional abnormality in the person, based on the conducting and the measuring, is determined. As a result of analysis of the brain electrical activity at rest and reactions and processing of stimuli, non-invasive brain stimulation takes place via said at least one anode electrode and said at least one cathode electrode to said brain of said person.

In embodiments of the above, a single electrode is surrounded by at least three electrodes. When the electrodes are used for stimulation purposes, the surrounding electrodes are of opposite polarity in a cluster. That is, an anode may be surrounded by three cathodes or a cathode may be surrounded three anodes. A plurality of such clusters may be utilized, such as by pre-placement in a helmet. Each cluster, or any single or plurality of electrodes, may be used to simultaneously or alternately stimulate different regions of the brain, based on the analysis described above.

The above-described analysis is augmented, in embodiments of the disclosed technology, based additionally on at least one additional measured/augmented physiological characteristic of a person. Such an additional measured/augmented physiological characteristic may be heart rate variability, a measure of balance, and measures of cognitive/peak performance, and pathology comparisons.

The conducting of non-invasive measurement of electrical currents, as well as the non-invasive brain stimulation, may be carried out by way of a single device with a single manually-operated control. Or, the control may be pre-configured and automated. That is, electric current in the brain may be measured, an anomaly discovered, and a pre-programmed non-invasive stimulation is then carried out in the same portion of the brain as the anomaly, and, in embodiments, using the same electrode or electrodes to stimulate as were used to measure.

In a system of embodiments of the disclosed technology, a joint brain electro-analysis and transcranial current stimulation system is made up of a plurality of spaced-apart removable and replaceable electrodes arranged in a piece of headgear, an electroencephalography device wired to each of the electrodes, and a transcranial current stimulation device wired to each of the electrodes. In this system, upon measuring an electroencephalography anomaly in a brain region with the electroencephalography device, transcranial current stimulation is engaged to at least one anode and at least one cathode electrode of the brain region where the anomaly was measured.

An additional (distinct and separate) device may be used for measuring physiological characteristics of a person wearing the piece of headgear. Such an additional device may measure heart rate variability, balance, cognitive impairment, and/or make pathology comparisons.

The electroencephalography device and the transcranial current stimulation device may be contained within a single housing, may be operable with a single set of controls, or may consist of separate devices requiring manual disconnection of a wire hub to the electrodes, and connection to the other device.

In accordance with these and other objects, which will become apparent hereinafter, the disclosed technology will now be described with particular reference to the drawings.

Figure 1:
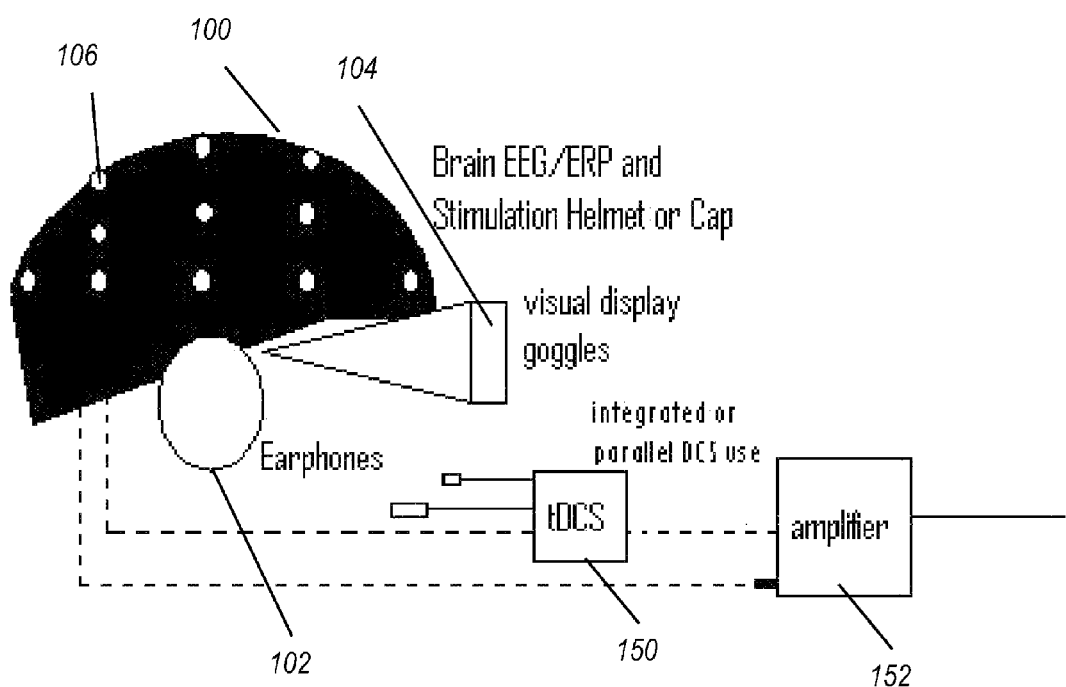
FIG. 1 shows a high level drawing of a device used to carry out embodiments of the disclosed technology.

A better understanding of the disclosed technology will be obtained from the following detailed description of the preferred embodiments taken in conjunction with the drawings and the attached claims.

DETAILED DESCRIPTION

Embodiments of the disclosed technology comprise systems and methods for assessing and repairing neurological pathways damaged by trauma or other brain-related dysfunction. The methods comprise training a patient and stimulating brain areas where a functional abnormality (such as abnormal electrical activity outside a threshold of voltage, regularity, coherence, phase, and/or rate) has been detected. Such functional abnormalities are determined based on electroencephalography testing, a physiological test that passively monitors electrical current of at least one electrode positioned over the head of a test subject.

Systems of the disclosed technology comprise the use of an electroencephalogram (EEG) which functions by recording electrical activity from the scalp. The EEG measures electrical activity produced by the firing of neurons within the brain. In addition, an event-related potential (ERP) measurement may be used. An ERP, for purposes of this disclosure is a measured brain response that is time locked to a stimulus presented to the subject.

Physiological tests/measurements may be any one of, or a combination of, the following, and are, for purposes of this disclosure, defined as follows: Transcranial current stimulation (tCS)—application of non-invasive current stimulation via at least one electrode which is also usable or used for EEG measurements in embodiments of the disclosed technology. For purposes of this disclosure, non-invasive current stimulation also refers to cranial electrotherapy stimulation (CES), which is defined as small pulses of electric current along the head of a subject.

Transcranial magnetic stimulation (TMS) is electromagnetic induction to induce weak electric currents using a rapidly changing magnetic field to cause activity in specific or general parts of the brain, and used for measurement of cortical or distance measures of EEG and EMG for evoked response latency.

Low threshold transcranial magnetic stimulation (lt-TMS) is electromagnetic frequency emitted by way of one or more sensors placed against the scalp to produce a focal field to cause activity in specific or general parts of the brain, and used for neuronal modulation.

Electromyography (EMG) are measurements of electrical potential of muscles.

Computerized neurophysiological testing (NP) is used to estimate a person's peak level of cognitive performance. A person's raw score on a test is compared to a large general population normative sample and/or to the subjects own baseline measurement.

Force platform or balance plate—a stand-on device usable to determine balance and/or vestibular dysfunction. The balance plate can collect and/or record balance and/or postural data, such as the center of pressure and sway movement to analyze vestibular and balance function under different test conditions (e.g., unstable foam pad and eyes closed). The velocity of movement or excursion from balance position can be quantified for comparison to database norms. For some embodiments, the balance plate can be moved without the need for recalibration, for example its use in outdoor settings (e.g., sports, military arena). Collected data can be synchronized by software contained in one or more computers, with visual input stimuli, EEG, ERP and/or other parameters for time-locked variance measures associated with brain dysfunction. For some embodiments, the balance plate may be operated by way of an electrical current connection and instructions carried out by way of a computing device (see FIG. 8) or alternatively with a wireless connection between the plate and the computing device for portable use.

Repetitive transcranial magnetic stimulation (rTMS) includes generating a magnetic field that influences electrical activity in the brain. In rTMS, passing current through a coil of wire generates the magnetic field, the current provided in a repetitive fashion.

Psychological disorder screening—(such as for post-traumatic stress disorder), a component for vestibulo-ocular reflex dysfunction, a component for heart rate variability measures, a component for electroencephalography measures, and/or a component for transcranial magnetic stimulation (TMS) delivery with voltage isolator for simultaneous amplified cortical and distally evoked potential latency measures and motor threshold measures.

By way of the above measurements, while non-invasively monitoring EEG readings of one or multiple sites/regions of the brain, anomalies in neurological impulses are detected. The sites or regions of the brain are then stimulated. As little as one sensor may be used to stimulate, and this anode or cathode may be at the site where the anomaly was detected and may be via the same electrode used to locate the anomaly and which measured the anomalous EEG/ERP measurement. Such an electrode may be in a helmet worn by a user and allows for positive (to increase neural activity) or negative (to decrease neural activity) stimulation at the site where the anomaly was detected.

Such embodiments of the disclosed technology will become clearer in view of the following description of the figures.

FIG. 1 shows a high level drawing of a device used to carry out embodiments of the disclosed technology. A helmet 100 comprises at least one, or a plurality of, electrodes 106 (represented as white dots). The helmet may be any receptacle which holds the electrodes in a position relative to the head of a wearer, or alternatively, electrodes may be taped or otherwise placed on the head. Earphones 102, goggles 104 and/or another display device are used in embodiments of the disclosed technology to exhibit stimuli to a user, the stimuli used to vary measurable brain activity. The electrodes 106 are electrically connected to one of an electrical stimulation device 150 or electrical measuring device (e.g., a sensor), such as by way of amplifier 152. The same electrode or electrodes may be disconnected from one such device and connected to another such device, such as by way of changing an electrical pathway (switch) or by physically disconnecting an electrical wire from one device, and plugging into another. In embodiments of the disclosed technology, the electrical stimulation and measuring devices are housed within the same physical device and comprise a switch for changing the electrical pathway, which is manually operated or controlled by pre-programmed instructions. In other embodiments, the measuring device and stimulation device are in separate housings or devices, and only one is electrically connected to the electrode or electrodes 106 at one time. In other embodiments, the electrical stimulation and measuring devices are housed within the same physical devise but have separate outlets to which the electrode(s) may be unplugged and attached. Other devices, not shown, include force platforms (measure postural deviations of person), devices to alter the display on the goggles 104, and devices to alter the sound through the earphones 102, and input devices such as a computer mouse, keyboards, and joysticks.

Referring now to visual stimuli exhibited on a display device, such as the goggles 104 of FIG. 1, the visual stimuli produced may be an "immersive environment," for example a virtual reality 2- or 3-dimension moving "room" displayed through a virtual reality headset. The data collected from the balance plate, heart rate monitor, EEG, and so forth, can be used in conjunction with the visual stimuli for neurophysiological trauma assessment and/or rehabilitation training. The data collected from this component, as well as all other components may be linked with data collected from other components (e.g., EEG, ERP) for assessment purposes.

The system shown in FIG. 1 may further comprise a vestibular activation test (VAT) headset permitting a computerized test that monitors the vestibulo-ocular reflex (VOR) during natural motion. A VAT headset useful for the systems described herein may produce images and/or record eye movements. Images displayed in the VAT headset may be generated by computer-implemented instructions and transmitted via electrical impulses to the VAT headset via wireless or direct connection. Eye movements may be recorded by way of the VAT headset. The VOR is a reflex eye movement that stabilizes images on the retina during head movement by producing an eye movement in the direction opposite to head movement, thus preserving the image on the center of the visual field. As ocular trauma is often concomitant with traumatic brain injury, this component allows additional assessment of injury.

Figure 2:
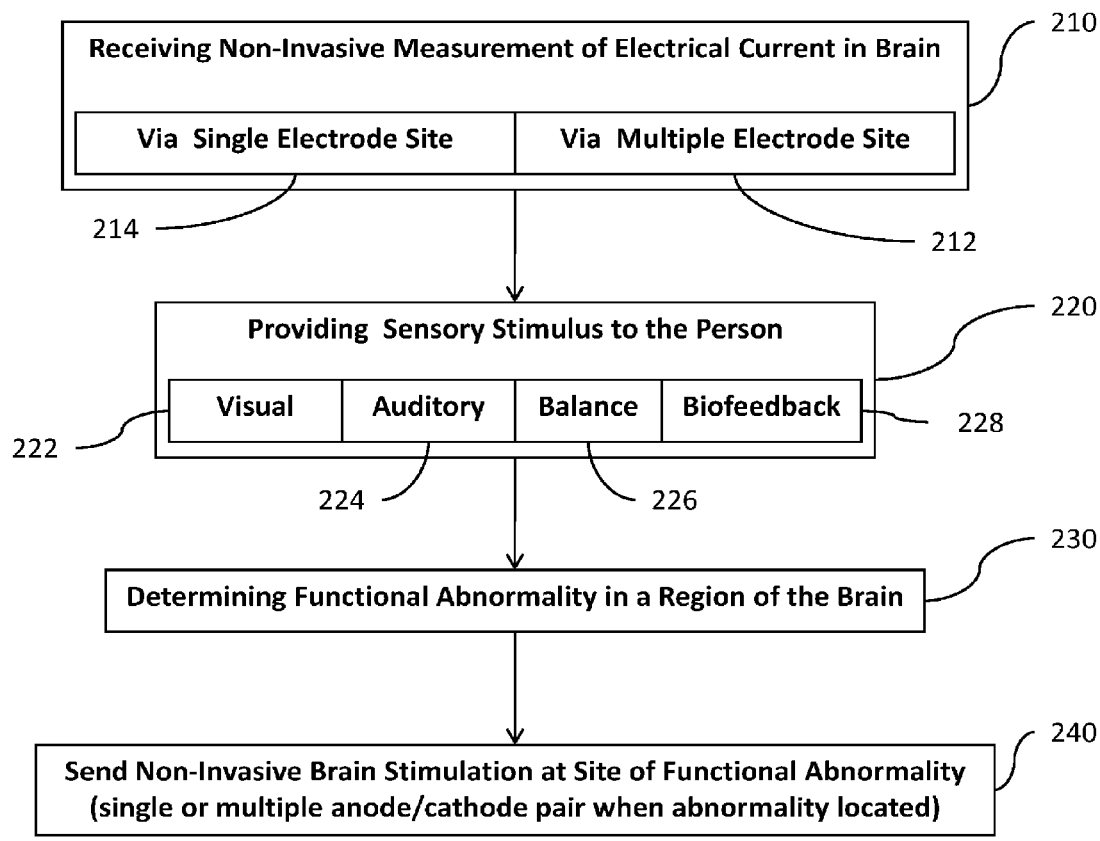
FIG. 2 shows a high level block diagram of a method of carrying out embodiments of the disclosed technology.

FIG. 2 shows a high level block diagram of a method of carrying out embodiments of the disclosed technology. In step 210, non-invasive measurements are made of electrical current in the brain of a test subject. This is accomplished by way of electrodes placed on a test subject, such as in a helmet shown in FIG. 1. In this manner, EEG and ERP signals may be recorded, measured, and analyzed. A single electrode may be used to carry out the measuring in step 214, or a plurality of electrode pairs may be used in step 212. The position of the electrodes is known, and each electrode or a grouping thereof is placed over a definable region of the brain, the region defined by a person carrying out embodiments of the disclosed technology. The region is defined as a specific brain area of interest for the recording, as defined by a person carrying out embodiments of the disclosed technology and may be a region covered by a single electrode pair or as large as half a hemisphere of a brain. Electrodes may also be grouped into clusters, such as with a single anode surrounded by three or more cathodes, or a single cathode surrounded by three or more anodes. Such clusters are electrically connected, such that electric current flows non-invasively through the proximal tissue from anode(s) to cathode(s), stimulating the brain (stimulating, herein is defined as passage of electrical current through the brain and includes increasing or decreasing neuron activity at a site).

While conducting step 210, typically, step 220 is also carried out which comprises providing sensory stimulus to a person. This may be done by way of, for example, the goggles shown in FIG. 1 for a visual stimulation 222, auditory stimulation 224, balance stimulation 226, biofeedback measurements 228, or other sensory stimulations known in the art. Definitions and examples of various types of such stimulations are provided above, before the description of the figures.

Stress tests and peak performance tests may also be performed to determine, for example, how many times a minute a person is able to respond to a stimulus, or how long a person can hold his/her breath or balance on a force platform, etc.

Based on the electrical measurements, that is, EEG or ERP measurements, an abnormality in a region of the brain is determined in step 230. An abnormality may be any of the following: electrical activity which is too infrequent, too frequent, too low in amplitude, too large in amplitude, an improper pattern of electrical activity, inter-intra-hemispheric connectivity, electrical activity in the wrong portion of the brain for the stimulus given, or the like.

In step 240, based on the located functional abnormality, non-invasive brain stimulation (such as tCS) is administered at the region of the abnormality. In certain cases, the same electrode which was used to measure the electrical impulses within the brain is used to administer tCS or other electrical stimulation. This tCS may be low intensity electromagnetic stimulation, such as rTMS technology or lt-TMS technology. In this manner, accuracy of the stimulated region may be assured, as there is no difference in the physical location on the head where the existing electrical impulse was measured, versus where the new electrical stimulation is administered. The place of administering may be as little as a single anode/cathode pair (or cluster), or may use multiple anode/cathode pairs (or clusters).

Figure 3:
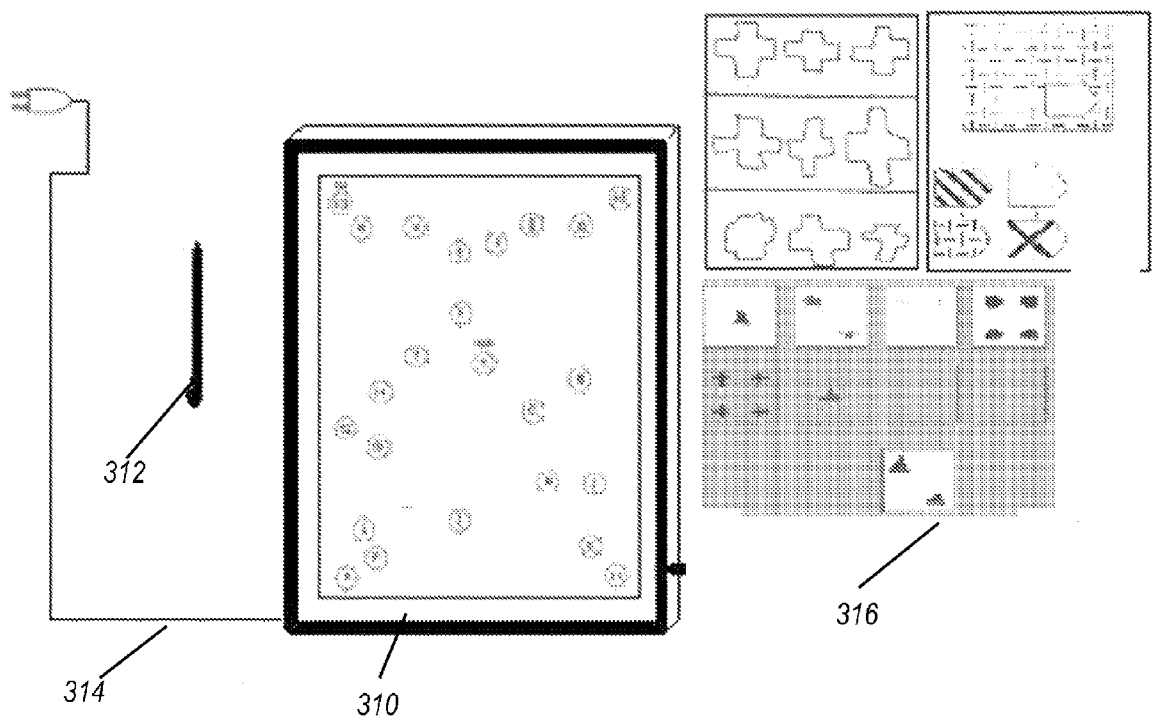
FIG. 3 shows an example of a test used to measure psychological characteristics of a test subject.

FIG. 3 shows an example of a test used to measure psychological characteristics of a test subject. The purpose of at least some of these tests is to assess the ability of the test subject to automatically and fluently perform relatively easy or overlearned cognitive tasks relevant to the ability to process information automatically or rapidly and measure executive function complex decision-making capacity. Tablet 310 is a device on which tests can be displayed (visual stimuli), such as various tests shown in 316. By using an input device, such as stylus 312, a user interacts with the visual display to carry out various functions. (The device may be powered via cord 314.) Such tests include, but are not limited to, trails making test, grooved pegboard, symbol-digit test, digit coding, symbol search, Stroop test, finger-tapping tests, categories test, Wonderlic tests and Wechsler subtests, Wisconsin Card Sort Test, matrix reasoning, Raven Progressive Matrices tests, and/or components of the neuropsychological assessment batteries. Still another type of test is a test of malingering (e.g., TOMM) which can be part of a comprehensive assessment of both mTBI (mild traumatic brain injury) and PTSD, as such tests aid in determining actual impairment resulting from neurophysiologic impairment as opposed to subject feigning or exaggerating. Such tests can assist in minimizing false positive mTBI diagnoses. Psychological questionnaires, for example a set of questions designed to diagnose a particular psychological disorder, such as PTSD, can also be included in computerized or hard copy form.

An additional component, a single pulse (0.9-1.5 tesla) fixed or variable Hz setting transcranial magnetic stimulation (TMS) device may be linked to a voltage isolator with linked amplifier for synchronized EEG, ERP and/or electromyogram (EMG) recordings or low threshold magnetic stimulation (lt-TMS) that operates independent of a voltage isolator. The amplifier (such as amplifier 152 of FIG. 1) may be a multichannel amplifier for multiple modality physiological measurements (e.g., EMG, ERP, EEG, temperature, blood volume pulse, respiration, skin conductance, EKG, blood pressure, etc.). Sensors for each physiological measurement may also be connected to the amplifier, for example as a means to collect measurements from a test subject. TMS is a non-invasive technique utilizing magnetic fields to create electric currents in discrete brain regions. Typically, during TMS, a time-pulsed magnetic field is focused on cortical tissue via a coil placed near the area to be affected (e.g., M1, Dorsolateral Prefrontal Cortex (DLPFC)). TMS can be utilized for various measurements of intracortical inhibition and facilitation, for example short interval intracortical inhibition (SICI), long interval intracortical inhibition (LICI) and contralateral cortical silent period (CSP). Such measurements can aid in differential diagnosis between individuals with mTBI and mTBI with PTSD. Any commercially available TMS device known in the art may be utilized. For some embodiments, the TMS device utilized is portable.

Low intensity electromagnetic stimulation has been shown to have certain and safe clinical value, with rTMS technology being one example. Low threshold stimulation below that of rTMS available in this device is called low threshold transcranial magnetic stimulation (lt-TMS). This electromagnetic stimulation is one of the methods utilized in this device yet with the added benefit of being able to apply such stimulation to one or more location points on the scalp within a given session or predesigned treatment sequence to stimulate along a neuronal network rather than one location along that network.

The lt-TMS is delivered using either a pulsed (or pulse-train) or sinusoidal electromagnetic stimulation waveform and is delivered based on the manual operation of the device or programmed delivery based on deviation measures from a normative or comparison database of collected EEG and ERPs produced by the same device. The device is designed to record electrophysiology allowing for a pre and post measure of such electrophysiology when utilizing any of the stimulation types within the device (tDCS, tACS, tRNS, lt-TMS).

While rTMS has limitations of stimulation rate below 20-30 Hz due to heat, the selection of lt-TMS within the device allows for longer session durations and faster stimulation.

In one embodiment, lt-TMS delivery can be performed manually at either one or multiple locations. Delivery at multiple locations can be done simultaneously or in timed preselected or preprogrammed sequence of locations. Another benefit of lt-TMS is the real time measuring of the electrophysiology before and after stimulation. The electrophysiology can also be measured as part of a preprogrammed stimulation sequence. Furthermore, lt-TMS electromagnetic stimulation permits longer stimulation durations without heating the neuronal tissue and with a larger range of frequency selections 0.1-100,000 Hz.

Figure 4:
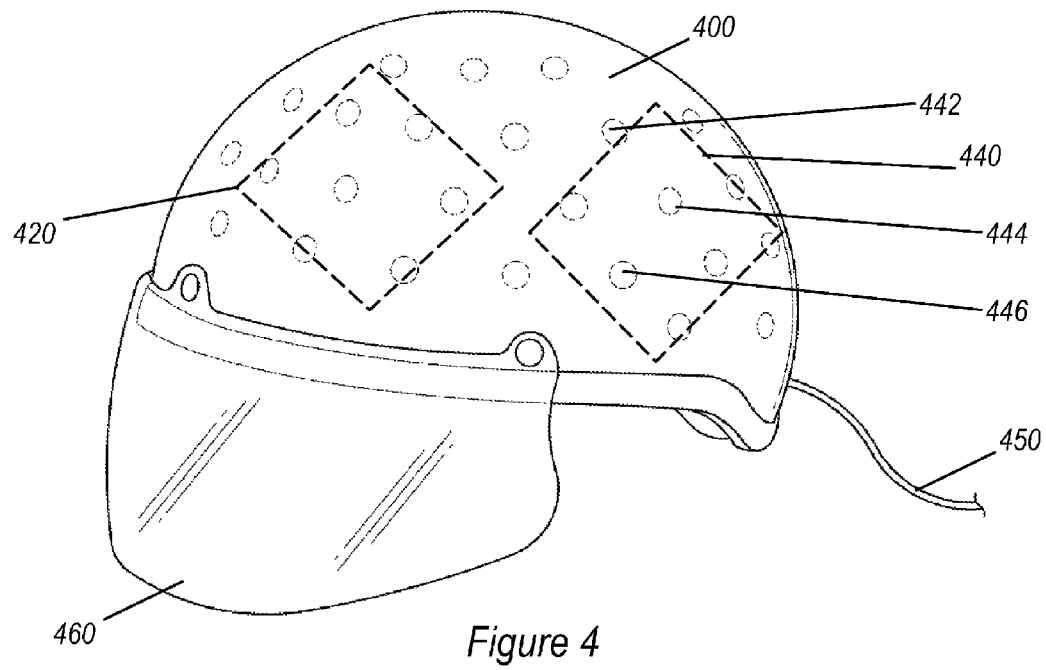
FIG. 4 shows a perspective view of a helmet with electrodes used in embodiments of the disclosed technology.
Figure 5:
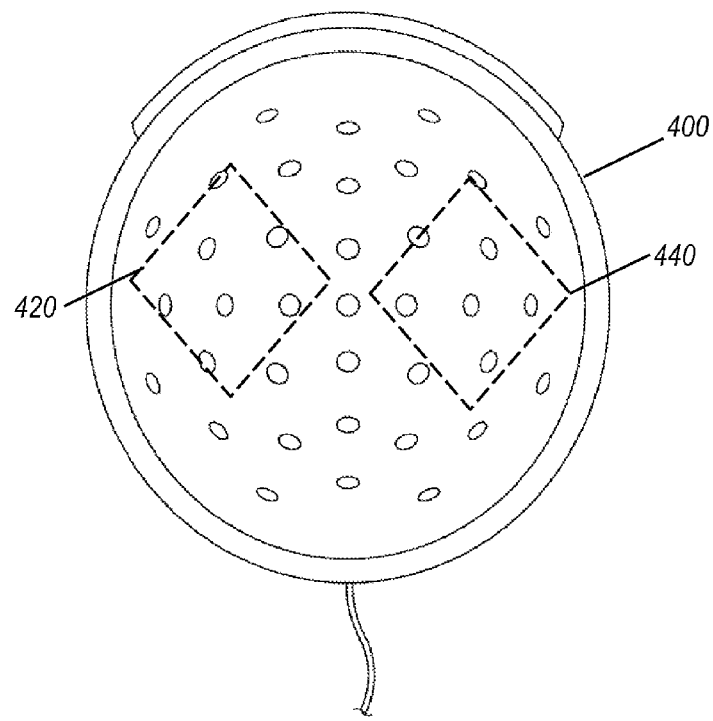
FIG. 5 shows a bottom view of a helmet with electrodes used in embodiments of the disclosed technology.

FIG. 4 shows a perspective view of a helmet with electrodes used in embodiments of the disclosed technology. FIG. 5 shows a bottom view of such a helmet. The helmet 400 comprises multiple electrodes, such as electrodes 442, 444, and 446. As can be seen in the figure, a plurality of electrodes are spaced apart around the interior of a helmet or other piece of headgear and are adapted for both reading electrical activity from the brain of the wearer and delivering new impulses. That is, by way of a single electrode, plurality thereof, cluster of electrodes, or plurality of clusters, a joint brain electroanalysis and transcranial current stimulation system (tCS) comprises a plurality of spaced-apart removable and replaceable electrodes arranged in an item of headgear. An electroencephalography device (such as an EEG) is wired to each of the electrodes, as is a transcranial current stimulation device (at the same time or alternating by way of a switch or plugging/unplugging a cable between the devices). In one embodiment, using lt-TMS, the stimulation sensors are smaller than conventionally larger (25-35 cm2) in order to provide both a quality electrophysiology measure and to deliver a more focal stimulation.

Due to the know dielectric propertied of skull and scalp tissue the device permits a dose-response adjustment such that the user can adjust frequency and intensity according to measured electrophysiology changes taken at the stimulation location or all scalp locations (e.g., EEG amplitude, EEG coherence, ERP amplitude and latency) and accordingly adjust stimulation thresholds to a level of desired neuronal tissue modulation.

A cable 450, which will be discussed at greater length with reference to FIG. 6, allows for electrical connectivity between the electrodes and either or both of a tCS and EEG device. Further, a viser 460 is integrated with the helmet in embodiments of the disclosed technology for optical stimulation (e.g. a video monitor). The device cap/helmet is constructed with an optional extension cable and materials such that simultaneous magnetic resonance imaging can occur while the device is in use.

Upon measuring an electroencephalography anomaly in a brain region with the electroencephalography device, transcranial current stimulation is engaged to at least one anode and at least one cathode electrode to the brain region where said anomaly was measured. Additional devices, as disclosed above, such as a force plate, visual stimuli utilizing interactive games and tests, and the like, may also be utilized. The transcranial current stimulation device, in embodiments of the disclosed technology, is engaged only when either a) data from the electroencephalography device indicates that electrical impulses in the brain are outside a predefined range/threshold of where they should be or where is desired by the administrator of the device; and/or b) when the additional physiological characteristic, as measured with another device disclosed in the specification herein (such as an EMG device, balance plate, pathological test, etc.) is out of range of a predefined allowable threshold. Thus, the ability to administer tDCS may be limited by the above factors and, as a safety measure, may be further limited automatically by way of pre-programmed instructions in a computer device (see FIG. 8) or manually by way of a physician or other clinical practitioner relying on such data.

The device delivers subthreshold polarization that potentially causes polarization at the soma and thereby obtains deeper brain source penetration and delivers a greater effect with a least intrusive and in a safer manner than high intensity stimulation. The device permits a programming of stimulation type (tDCS, tACS, tRNS, lt-TMS) delivery interrupted by electrophysiology measures (e.g., EEG, ERPs) in order to ascertain the relative difference each stimulation type has on neuronal activation or suppression such that the most efficient and effective intervention can be then applied for the individual.

Referring further to a force plate (which includes a "balance plate" in embodiments of the disclosed technology), the device is used as follows. The force plate collects (and may record) balance and/or postural data, such as center of pressure, sway movement, and movement velocity to analyze vestibular and balance function under different test conditions (e.g., unstable foam pad and eyes closed). For some embodiments, the balance plate may be moved without the need for recalibration, for example use in outdoor settings (e.g., sports, military arena). Collected data may be synchronized with visual input stimuli, EEG, ERP and/or other parameters for time locked variance measures associate with brain dysfunction. In some instances, visual stimuli are provided to a subject while the subject utilizes the force plate. The visual stimuli produced may be an "immersive environment", for example a virtual reality 2- or 3-dimension moving "room" displayed through a virtual reality headset. The data collected from the force plate is used, in embodiments of the disclosed technology, for neurophysiological trauma assessment and/or rehabilitation training.

As further seen in FIG. 4, the anodes and cathodes may be in a cluster 420 and 440. The clusters shown are by way of example. That is, one anode (e.g., 444) may be surrounded by three or more cathodes (e.g., 442, 446, and others), or one cathode may be surrounded by three or more anodes. Anodes and cathodes have opposite polarity, and where neural activity is too high in a region, a cathode may be used to suppress activity. Where neural activity is too low in a region, an anode may be used to increase activity. This may be done between two electrodes, a cluster, or a plurality of clusters. In two different regions, it may be desired, in embodiments of the disclosed technology, to stimulate (or de-stimulate) simultaneously. In this context, "simultaneously" may be defined as being at the same time or alternating. Different rates of stimulation at each region may also be used, as necessary. That is, two regions that should not be linked, in fact are. By firing at different times or rates, in different regions (at the second region, firing from 0 to 180 degrees off, in a phase between two firings of the first electrode), two synced regions may be brought out of phase. This may normalize brain activity as regions of the brain require specific phase similarities and differences depending upon their relative function. Similarly, by firing at the same time, two out of sync regions may be brought in phase. Now, the two regions are said to have coherence. Biofeedback (a user viewing his/her own EKG, EEG, ERP, or other indicators of physiology function) may be utilized in conjunction with the tDCS, so as to give the user the ability to consciously control his or her brain or other physiological activity to help the healing process when attempting to normalize brain or physiological function (e.g., heart rate variability) activity.

The electrodes may be separable, so as to be individually placed, or may be within a sized EEG cap or helmet (such as helmet 100 of FIG. 1). The electrodes, which can also be used as anodes and cathodes for purposes of tDCS, may be directly connected to one or more stimulation devices (e.g., tDCS or CES stimulation) and/or measuring devices (e.g., EEG recording device) simultaneously, or via a switch or removable plug to switch between such devices. When measuring EEG/ERP readings (electrical impulses from the brain of a user), various activities (stimuli or physiological measurements) may take place simultaneously. A finger depression device may be used, and others such as a force platform, heart rate monitor, EMG (muscle electric potential), interactive biofeedback devices allowing the user to monitor internal activity (directly or by way of a game used to control by way of biofeedback), and the like. These measurements may then be compared against a database of known human population normative values as indications to determine a deviation from normal function, check the deviation against what is being monitored by way of EEG measures and abnormalities of electric impulses in the brain, and in some embodiments, a correlation may be made to determine brain abnormalities associated with different dysfunctions. In other embodiments, the brain abnormalities will serve to verify a particular dysfunction. In still further embodiments, based on prior determined data of brain electrical abnormalities for a specific pathology, tDCS or other electrical stimuli (e.g., CES) is then induced at a region where the brain abnormality is measured.

For example, a database may contain reference EEG components for normal and known pathological results (e.g., IED blast brain trauma, motor vehicle accident brain trauma, Attention Deficit Disorder, Alzheimer's disease). In some instances a database may comprise subcategorization of data from collected EEG and ERP data. Comparison of subject EEG and ERP results to such databases can allow for EEG and ERP analysis as part of the diagnostic process. Source localization methods (to determine specific regions of interest and dysfunction) may be accessed for selected EEG and ERP components.

When transcranial current stimulation (tCS) is used as a result of the above measures, the current may be via the EEG electrodes or can be delivered by other anode and cathode electrodes (i.e., anode sensors or cathode sensors placed from a different system) designated for tCS treatment. For example, sponges may be attached to graphite composite sensor pads sized for anode and/or cathode to ensure proper contact with the subject. The tCS device, in embodiments of the disclosed technology, directs anodal or cathodal non-invasive brain stimulation to one or more of the connected site locations on the subject. Stimulation can be delivered as transcranial current, or other effective current type, in amounts between about 0.25 mA and 6.0 mA.

Figure 6:
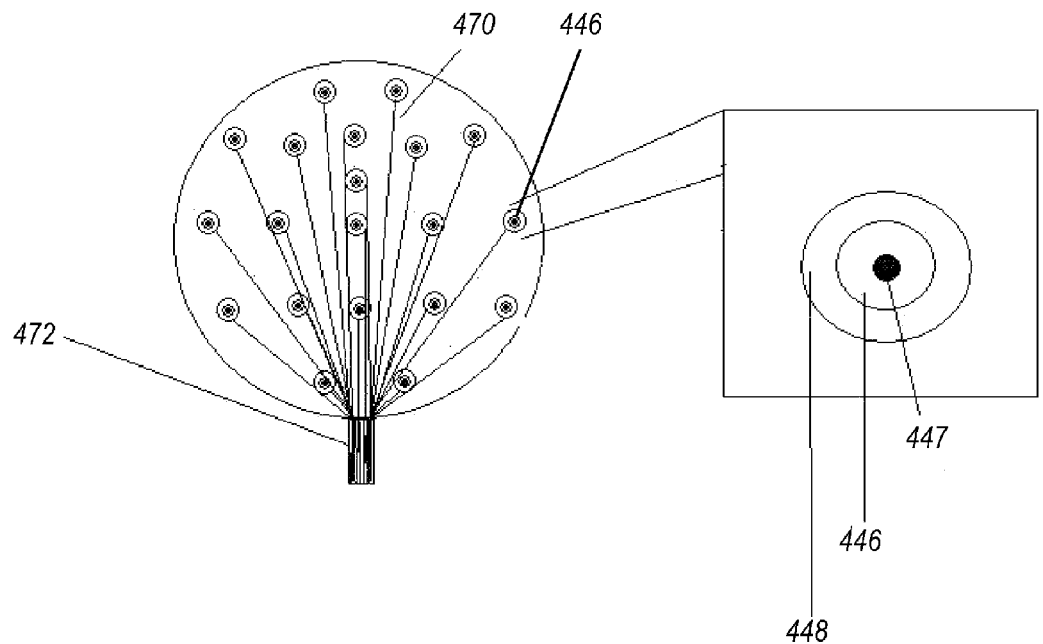
FIG. 6 shows electrical pathways to electrodes within a helmet of an embodiment of the disclosed technology.

FIG. 6 shows electrical pathways to electrodes within a helmet of an embodiment of the disclosed technology. Electrical connections (such as connection 470) provide an electrical pathway to and from each electrode and join at a cable 472 housing all electrical connectors between each electrode and an amplifier or other equipment for sending and/or receiving electrical impulses. Each electrode, such as electrode 446 comprises the electrode itself (typically, a metal or other known conductor, the conductor being removable from an electrode housing 448 with disposable electrode boot 449 in embodiments of the disclosed technology) with a hole 447 for inserting conductive gel.

Figure 7:
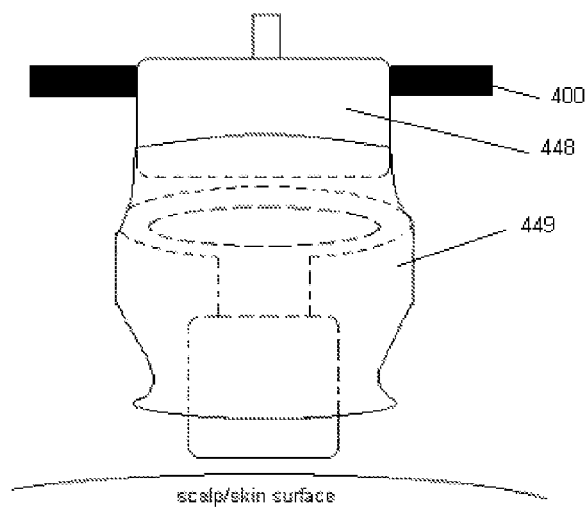
FIG. 7 is a side view of an electrode with disposable electrode boot attachment used in an embodiment of the disclosed technology.

FIG. 7 is a side view of an electrode with disposable electrode boot used in an embodiment of the disclosed technology. An encasement 448, such as one made of hard plastic covers the electrode. The electrode 449 is attached within the helmet 400. A disposable foam conductive patch is inserted, in embodiments of the disclosed technology, into an electrode sensor. Conductive gel permits a conductive connection from the electrode, and by extension the foam patch insert, to the skin. This connection permits both the recording of cortical electrical activity and the delivery of anodal or cathodal direct current. Two version of this electrode are available: (1) The first version is a soft rubber boot that can be wrapped around a hard plastic electrocap device. This soft boot slips onto any of the electrocap sensors and has within it a porous foam or sponge pad. The connective gel that is inserted into the electrocap hole also flows into this boot as shown in the art. (2) A second version is a harder plastic, carbon, or graphite material replacement sensor that connects to any wire harness for EEG/ERP and may be built into a helmet or softer cap.

In an embodiment of the disclosed technology, a single interface is used to control EEG, ERP, and tCS and is electrically or wirelessly connected/engaged with any one of or a plurality of inputs including ECG sensors, a balance plate, a headset, a tCS cap, or the like. Between the input devices and the interface may be a voltage isolator and/or amplifier. The interface, or a separate computational device (See FIG. 8), may be used for data collection and analysis from the EEG/ERP cap and other inputs. Visual images may be displayed on a headset and visual and auditory stimuli may be provided by way of a monitor and speakers, respectively.

Figure 8:
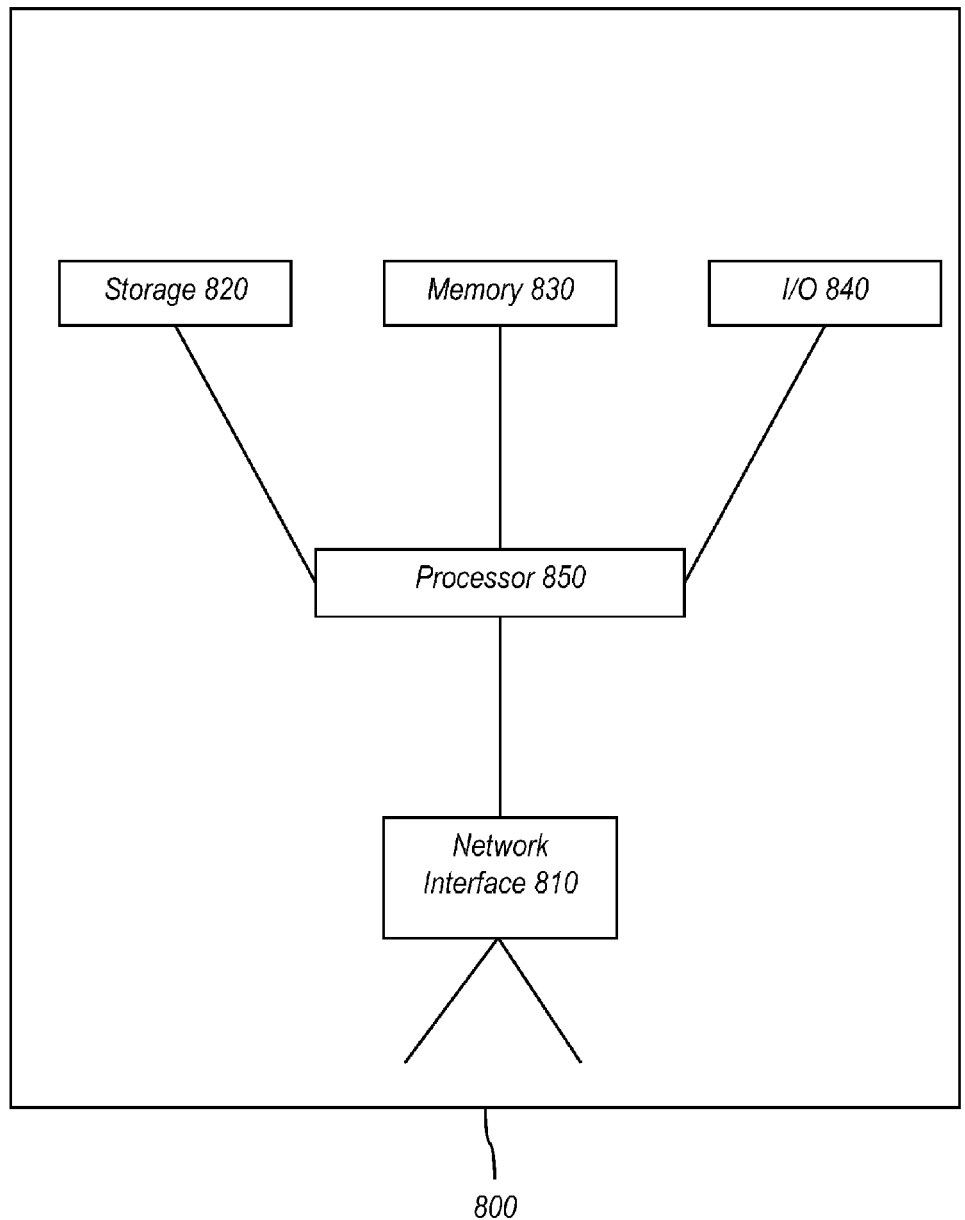
FIG. 8 is a high-level block diagram of a bidirectional transceiver that may be used to carry out the disclosed technology.

FIG. 8 is a high-level block diagram of a computational device that may be used to carry out the disclosed technology. Computer device 800 comprises a processor 850 that controls the overall operation of the computer by executing the entered program instructions, which define such operation. The program instructions may be stored in a storage device 820 (e.g., magnetic disk, database) and loaded into memory 830 when execution of program instructions is desired. Thus, the computer's operation will be defined by the program instructions stored in memory 830 and/or storage 820, and the console will be controlled by processor 850 executing the program instructions. A computer 800 also includes one or a plurality of input network interfaces for communicating with other devices via a network (e.g., the Internet). The computer 800 further includes an electrical input interface for receiving power and data from a wired or wireless source. A computer 800 also includes one or more output network interfaces 810 for communicating with other devices. Computer 800 also includes input/output 840 representing devices, which allow for user interaction with a computer (e.g., display, keyboard, mouse, speakers, buttons, stylus, etc.). One skilled in the art will recognize that an implementation of an actual device will contain other components as well, and that FIG. 8 is a high level representation of some of the components of such a device for illustrative purposes. It should also be understood by one skilled in the art that the method and devices depicted in FIGS. 1 through 7 may be implemented on a device such as is shown in FIG. 8.

While the disclosed technology has been taught with specific reference to the above embodiments, a person having ordinary skill in the art will recognize that changes can be made in form and detail without departing from the spirit and the scope of the disclosed technology. The described embodiments are to be considered in all respects only as illustrative and not restrictive. All changes that come within the meaning and range of equivalency of the claims are to be embraced within their scope. Combinations of any of the methods, systems, and devices described hereinabove are also contemplated and within the scope of the disclosed technology.

What is claimed is:

1. A bi-directional method of carrying out electrophysiological data recording and analysis with delivery of transcranial current stimulation, comprising:
   via at least one electrode, providing current stimulation of electrical currents within a brain of a person, the at least one electrode including at least one anode electrode and at least one cathode electrode, the current of the current stimulation being at least one of: direct current and alternating current;
   via at least one electrode, conducting a non-invasive measurement of the electrical currents within the brain of the person;
   determining an anomaly in the brain of the person based on the conducting the non-invasive measurement while the person receives sensory stimuli;
   sending a non-invasive brain stimulation via said at least one anode and said at least one cathode electrode to said brain of said person; and
   augmenting the non-invasive stimulation based on at least one measured physiological characteristic of the person.

2. The method of claim 1, further comprising:
   conducting non-invasive measurements of electrical currents via a plurality of electrode pairs.

3. The method of claim 2, wherein the electrode pair comprises a cluster of a single electrode surrounded by at least three electrodes of opposite polarity to the single electrode.

4. The method of claim 3, wherein the non-invasive brain stimulation comprises sending the non-invasive brain stimulation using a plurality of clusters of electrodes.

5. The method of claim 4, wherein all the clusters simultaneously stimulate a different region of the brain based on the analysis.

6. The method of claim 4, wherein each of the clusters alternately stimulate a different region of the brain based on the analysis.

7. The method of claim 4, wherein the plurality of electrodes is prearranged in a single piece of headgear worn by the person.

8. The method of claim 1, wherein the additional measured physiological characteristics is selected from the group consisting of heart rate variability, a measure of neuropathway speed and amplitude, a measure of balance, measures of peak performance, and pathology comparisons.

9. The method of claim 1, wherein the conducting and the sending are carried out by way of a pre-configured automated process.

10. The method of claim 1, wherein the anomaly is a functional abnormality in the brain of the person.

11. A joint brain electro-analysis and transcranial current stimulation system comprising:
a plurality of spaced-apart removable and replaceable at least one of: electrodes and sensors, arranged in a piece of headgear;
an electroencephalography device wired to one or more of said at least one of: electrodes and sensors;
a transcranial current stimulation device wired to one or more of said electrodes, wherein said electrodes are configured for conducting non-invasive measurements of a person; and
wherein, upon determining an anomaly in the brain of the person based on the conducting the non-invasive measurement, while the person receives a sensory stimuli, the current stimulation device sends a non-invasive brain stimulation via said at least one anode and said at least one cathode electrode to the brain of said person and augmenting the non-invasive stimulation based on at least one measured physiological characteristic of the person.

12. The joint brain electro-analysis and transcranial current stimulation system of claim 1 further comprising: a headgear including a plurality of the electrodes, wherein said plurality of the electrodes includes electrode pairs configured for conducting non-invasive measurements of electrical currents via the plurality of electrode pairs.

13. The joint brain electro-analysis and transcranial current stimulation system of claim 12, wherein the electrode pair comprises a cluster of a single electrode surrounded by at least three electrodes of opposite polarity to the single electrode.

14. The joint brain electro-analysis and transcranial current stimulation system of claim 13, wherein the non-invasive brain stimulation includes sending the non-invasive brain stimulation using at least one of the plurality of clusters of the single electrode surrounded by the at least three electrodes of opposite polarity.

15. The joint brain electro-analysis and transcranial current stimulation system of claim 11 further comprising:
an additional device for measuring physiological characteristics of the person wearing the piece of headgear.

16. The joint brain electro-analysis and transcranial current stimulation system of claim 11, wherein the transcranial current stimulation device is engaged only when said additional physiological characteristic is out of range of a predefined allowable threshold.

17. The joint brain electro-analysis and transcranial current stimulation system of claim 11, wherein said additional measured physiological characteristic is selected from the group consisting of heart rate variability, a measure of balance, a measure of at least one of functional cortical brain networks and structural cortical brain networks, a measure of event related potentials, measures of peak performance, and pathology comparisons.

18. The joint brain electro-analysis and transcranial current stimulation system of claim 11, wherein the transcranial current stimulation consists of one or more of: pulsed transcranial direct current stimulation, non-pulsed transcranial direct current stimulation, transcranial alternating current stimulation and transcranial random noise current stimulation.

19. The joint brain electro-analysis and transcranial current stimulation system of claim 11, wherein the anomaly is a functional abnormality in the brain of the person.

* * * * *

UNITED STATES PATENT AND TRADEMARK OFFICE
CERTIFICATE OF CORRECTION

| | | |
|---|---|---|
| PATENT NO. | : 8,942,813 B1 | Page 1 of 1 |
| APPLICATION NO. | : 14/516207 | |
| DATED | : January 27, 2015 | |
| INVENTOR(S) | : Hagedorn et al. | |

It is certified that error appears in the above-identified patent and that said Letters Patent is hereby corrected as shown below:

Claims

Col. 14, line 2, Claim 12: replace "system of claim 1" with "system of claim 11".

Signed and Sealed this
Seventeenth Day of November, 2015

Michelle K. Lee
*Director of the United States Patent and Trademark Office*